US008105363B2

(12) United States Patent
Fielding et al.

(10) Patent No.: US 8,105,363 B2
(45) Date of Patent: *Jan. 31, 2012

(54) SPINAL IMPLANT AND METHOD FOR RESTRICTING SPINAL FLEXION

(75) Inventors: Louis Fielding, Portland, OR (US); Ian Bennett, Portola Valley, CA (US); Colin Cahill, Stanford, CA (US); Pat Arensdorf, Palo Alto, CA (US); Ralph Crisostomo, Rochester, MN (US); Todd Alamin, Woodside, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 213 days.

This patent is subject to a terminal disclaimer.

(21) Appl. No.: 12/364,487

(22) Filed: Feb. 2, 2009

(65) Prior Publication Data
US 2009/0198282 A1    Aug. 6, 2009

Related U.S. Application Data

(60) Continuation of application No. 12/262,877, filed on Oct. 31, 2008, which is a division of application No. 11/076,469, filed on Mar. 9, 2005, now Pat. No. 7,458,981.

(60) Provisional application No. 60/551,235, filed on Mar. 9, 2004.

(51) Int. Cl.
*A61B 17/88* (2006.01)
(52) U.S. Cl. ......................... 606/279; 606/249
(58) Field of Classification Search .......... 606/248–249, 606/279
See application file for complete search history.

(56) References Cited

U.S. PATENT DOCUMENTS

| 3,648,691 A | 3/1972 | Lumb et al. |
| 4,246,660 A | 1/1981 | Wevers |
| 4,643,178 A | 2/1987 | Nastari et al. |
| 4,708,132 A | 11/1987 | Silvestrini |
| 4,743,260 A | 5/1988 | Burton |
| 4,772,286 A | 9/1988 | Goble et al. |
| 4,776,851 A | 10/1988 | Bruchman et al. |
| 4,794,916 A | 1/1989 | Porterfield et al. |
| 4,870,957 A | 10/1989 | Goble et al. |
| 4,955,910 A | 9/1990 | Bolesky |
| 4,966,600 A | 10/1990 | Songer et al. |

(Continued)

FOREIGN PATENT DOCUMENTS
EP    0322334 A1    6/1989

(Continued)

OTHER PUBLICATIONS

Al Baz et al.; Modified technique of tension band wiring in flexion injuries of the middle and lower cervical spine; Spine; vol. 20; No. 11; pp. 1241-1244; 1995.

(Continued)

*Primary Examiner* — Nicholas Woodall
(74) *Attorney, Agent, or Firm* — Shay Glenn LLP

(57) ABSTRACT

A spinal implant system for restricting flexion of a spine includes an elongate band proportioned to engage at least two spinous processes. During use, the band is positioned engaging the spinous processes at a spinal segment of interest, where it restricts flexion at the segment. The length and tension of the band may be adjustable following to implantation using percutaneous or transcutaneous means.

29 Claims, 11 Drawing Sheets

U.S. PATENT DOCUMENTS

| | | |
|---|---|---|
| 5,002,574 A | 3/1991 | May et al. |
| 5,011,484 A | 4/1991 | Breard |
| 5,011,494 A | 4/1991 | Von Recum et al. |
| 5,030,220 A | 7/1991 | Howland |
| 5,092,866 A | 3/1992 | Breard et al. |
| 5,108,433 A | 4/1992 | May et al. |
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,366,455 A | 11/1994 | Dove et al. |
| 5,387,213 A | 2/1995 | Breard et al. |
| 5,395,374 A | 3/1995 | Miller et al. |
| 5,415,658 A | 5/1995 | Kilpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,593,407 A | 1/1997 | Reis |
| 5,609,634 A | 3/1997 | Voydeville |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A | 3/1998 | Bevan et al. |
| 5,810,815 A | 9/1998 | Morales |
| 5,836,948 A | 11/1998 | Zucherman et al. |
| 5,902,305 A | 5/1999 | Beger et al. |
| RE36,221 E | 6/1999 | Breard et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,290,724 B1 | 9/2001 | Marino |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 | 5/2002 | Castaneda |
| 6,427,080 B1 | 7/2002 | Radak |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 | 6/2003 | Yun |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,899,716 B2 | 5/2005 | Cragg |
| 6,989,011 B2 | 1/2006 | Paul et al. |
| 7,029,475 B2 | 4/2006 | Panjabi |
| 7,163,558 B2 | 1/2007 | Senegas et al. |
| 7,201,751 B2 | 4/2007 | Zucherman et al. |
| 7,335,203 B2 | 2/2008 | Winslow et al. |
| 7,413,576 B2 | 8/2008 | Sybert et al. |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow et al. |
| 7,553,320 B2 | 6/2009 | Molz, IV et al. |
| 7,591,837 B2 | 9/2009 | Goldsmith |
| 2001/0007073 A1 | 7/2001 | Zucherman et al. |
| 2002/0151978 A1 | 10/2002 | Zacouto et al. |
| 2003/0050700 A1 | 3/2003 | Kihara |
| 2003/0088251 A1 | 5/2003 | Braun et al. |
| 2004/0024458 A1 | 2/2004 | Senegas et al. |
| 2004/0034351 A1 | 2/2004 | Sherman et al. |
| 2004/0082954 A1 | 4/2004 | Teitelbaum et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0243239 A1 | 12/2004 | Taylor |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0154390 A1 | 7/2005 | Biedermann et al. |
| 2005/0192581 A1 | 9/2005 | Molz et al. |
| 2005/0203624 A1 | 9/2005 | Serhan et al. |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0069447 A1 | 3/2006 | DiSilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell et al. |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0173818 A1 | 7/2007 | Hestad et al. |
| 2007/0213829 A1 | 9/2007 | Le Couedic et al. |
| 2008/0009866 A1 | 1/2008 | Alamin et al. |
| 2008/0027435 A1 | 1/2008 | Zucherman et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 | 10/2008 | Bennett et al. |
| 2009/0030457 A1 | 1/2009 | Janowski et al. |
| 2009/0082820 A1 | 3/2009 | Fielding et al. |
| 2009/0118766 A1 | 5/2009 | Park et al. |
| 2009/0198282 A1 | 8/2009 | Fielding et al. |
| 2009/0264929 A1 | 10/2009 | Alamin et al. |
| 2009/0264932 A1 | 10/2009 | Alamin et al. |
| 2010/0004701 A1 | 1/2010 | Malandain et al. |
| 2010/0023060 A1 | 1/2010 | Bennett et al. |
| 2010/0036424 A1 | 2/2010 | Fielding et al. |
| 2010/0234890 A1 | 9/2010 | Alamin et al. |
| 2010/0234894 A1 | 9/2010 | Alamin et al. |
| 2010/0249839 A1 | 9/2010 | Alamin et al. |

FOREIGN PATENT DOCUMENTS

| | | |
|---|---|---|
| EP | 0743045 A2 | 11/1996 |
| FR | 2681525 A1 | 3/1993 |
| FR | 2693364 A1 | 1/1994 |
| FR | 2714591 A1 | 7/1995 |
| FR | 2717675 A1 | 9/1995 |
| FR | 2722980 A1 | 2/1996 |
| FR | 2851154 A1 | 8/2004 |
| FR | 2874167 A1 | 2/2006 |
| WO | WO 9942051 A1 * | 8/1999 |
| WO | WO 01/28442 A1 | 4/2001 |
| WO | WO 02/03882 A2 | 1/2002 |
| WO | WO 02/051326 A1 | 7/2002 |
| WO | WO 02/071960 A1 | 9/2002 |
| WO | WO 03/045262 A2 | 6/2003 |
| WO | WO 2004/052246 A1 | 6/2004 |
| WO | WO 2004/073532 A1 | 9/2004 |
| WO | WO 2004/073533 A1 | 9/2004 |
| WO | WO 2005/037150 A1 | 4/2005 |
| WO | WO 2005/110258 A1 | 11/2005 |
| WO | WO 2008/051423 A1 | 5/2008 |
| WO | WO 2008/051801 A2 | 5/2008 |
| WO | WO 2008/051802 A2 | 5/2008 |
| WO | WO 2008/051806 A2 | 5/2008 |
| WO | WO 2009/149407 A9 | 12/2009 |
| WO | WO 2010/028165 A8 | 3/2010 |

OTHER PUBLICATIONS

Dickman et al.; Comparative mechanical properties of spinal cable and wire fixation systems; Spine; vol. 22; No. 6; pp. 596-604; Mar. 15, 1997.

Garner et al.; Development and preclinical testing of a new tension-band device for the spine: the loop system; European Spine Journal; vol. 11; supp. 2; pp. S186-S191; 2002.

Heller; Stability of different wiring techniques in segmental spinal instrumentation. An experimental study; Archives of Orthopedic and Trauma Surgery; vol. 117; No. 1-2; pp. 96-99; Nov. 1997.

Leahy et al.; Design of spinous process hooks for flexible fixation of the lumbar spine; Proceedings of the Institution of Mechanical Engineers, Part H; Journal of Engineering in Medicine; vol. 214; No. 5; pp. 479-487; Sep. 27, 2000.

Leahy et al.; Mechanical testing of a flexible fixation device for the lumbar spine; Proceeding of the Institution of Mechanical Engineers, Part H; Journal of Engineering in Medicine; vol. 214; No. 5; pp. 489-495; Sep. 27, 2000.

Minns et al.; Preliminary design and experimenatal studies of a novel soft implant for correcting sagittal plane instability in the lumbar spine; Spine; vol. 22; No. 16; pp. 1819-1825; Aug. 15, 1997.

Miyasaka et al.; Radiographic analysis of lumbar motion in relation to lumbosacral stability: Investigation of moderate and maximum motion; Spine; vol. 25; No. 6; pp. 732-737; Mar. 15, 2000.

Papp et al.; An in vitro study of biomechanical effects of flexible stabiliation on the lumbar spine; Spine; vol. 22; No. 2; pp. 151-155; Jan. 15, 1997.

Shepard et al.; Spinous process strength; Spine; vol. 25; No. 3; pp. 319-323; Feb. 1, 2000.

Shepard et al.; Slippage of a spinous process hook during flexion in a flexible fixation system for the lumbar spine; Medical Engineering and Physics; vol. 23; No. 2; pp. 135-141; Mar. 2001.

Voydeville et al.; Ligamentoplastie intervertebrale avec cale souple dans les instabilities lombaries; <<Intervertebral ligamentoplasty with flexible wedge in lumbar instability>>; Orthop. Traumatol.; vol. 2; pp. 259-264; 1992.

Abbott Spine; Wallis Surgical Technique; The Art & Science of Spine Surgery; Product brochure; 22 pgs.; 2006.

Brinckmann et al.; Mechanical aspects of the lumbar spine; Theime Stuttgart—New York; Chapter 11; pp. 105-128; 2002.

Frymoyer et al.; An overview of the incidences and costs of low back pain; Ortho. Clin. North Am.; vol. 22; No. 2; pp. 263-271; Apr. 1991.

Medtronic Sofamor Danek USA, Inc.; DIAM system implants; Product brochure; 20 pgs.; 2006.

* cited by examiner

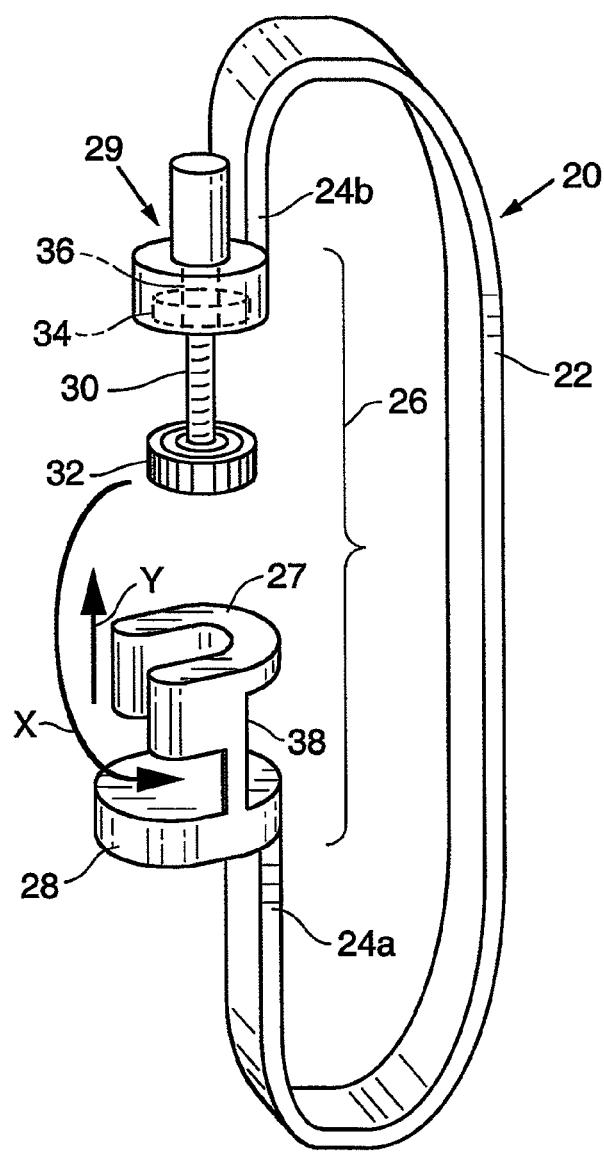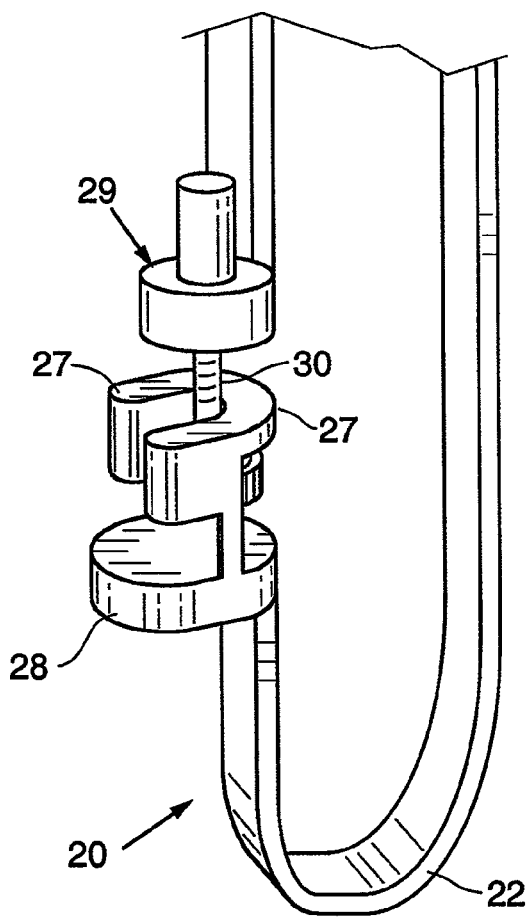
FIG. 3A
FIG. 3B

SPINAL IMPLANT AND METHOD FOR RESTRICTING SPINAL FLEXION

CROSS REFERENCE TO RELATED APPLICATIONS

This application is a continuation, of U.S. patent application Ser. No. 12/262,877, filed Oct. 31, 2008, titled "SPINAL IMPLANT AND METHOD FOR RESTRICTING SPINAL FLEXION", which is a divisional of U.S. patent application Ser. No. 11/076,469, filed Mar. 9, 2005, now U.S. Pat. No. 7,458,981, titled "SPINAL IMPLANT AND METHOD FOR RESTRICTING SPINAL FLEXION", which claims the benefit under 35 U.S.C. 119 of U.S. Patent Application No. 60/551,235 filed Mar. 9, 2004, titled "DEVICES THAT TREAT BACK PAIN AND STABILIZE THE SPINE".

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to the field of spinal implants and more particularly to the field of implants for restricting spinal flexion.

BACKGROUND OF THE INVENTION

A major source of chronic low back pain is discogenic pain, which is also known as internal disc disruption. Patients suffering from discogenic pain tend to be young (30-50 years of age), otherwise healthy individuals who present with pain localized to the back. Usually discogenic pain occurs at the discs located at the L4-L5 or L5-S1 junctions. Pain tends to be exacerbated when patients put their lumbar spines into flexion (i.e. by sitting or bending forward) and relieved when they put their lumbar spines into extension (i.e. arching backwards). Discogenic pain can be quite disabling, and for some patients it dramatically affects their ability to work and otherwise enjoy their lives.

Current treatment alternatives for patients diagnosed with chronic discogenic pain are quite limited. Many patients continue with conservative treatment (examples include physical therapy, massage, anti-inflammatory and analgesic medications, muscle relaxants, and epidural steroid injections) and live with a significant degree of pain. Others elect to undergo spinal fusion surgery, which typically involves discectomy (removal of the disk) together with fusion of adjacent vertebrae. Fusion is not typically recommended for discogenic pain because it is irreversible, costly, associated with high morbidity, and of questionable effectiveness. Despite its drawbacks, however, spinal fusion for discogenic pain remains common due to the lack of viable alternatives.

BRIEF DESCRIPTION OF THE DRAWINGS

FIG. 3A is a perspective view of the spinal implant of FIG. 2 in an opened position.
FIG. 3B is a perspective view of the spinal implant of FIG. 2 in a closed position.

DETAILED DESCRIPTION OF THE INVENTION

Figure 1A:
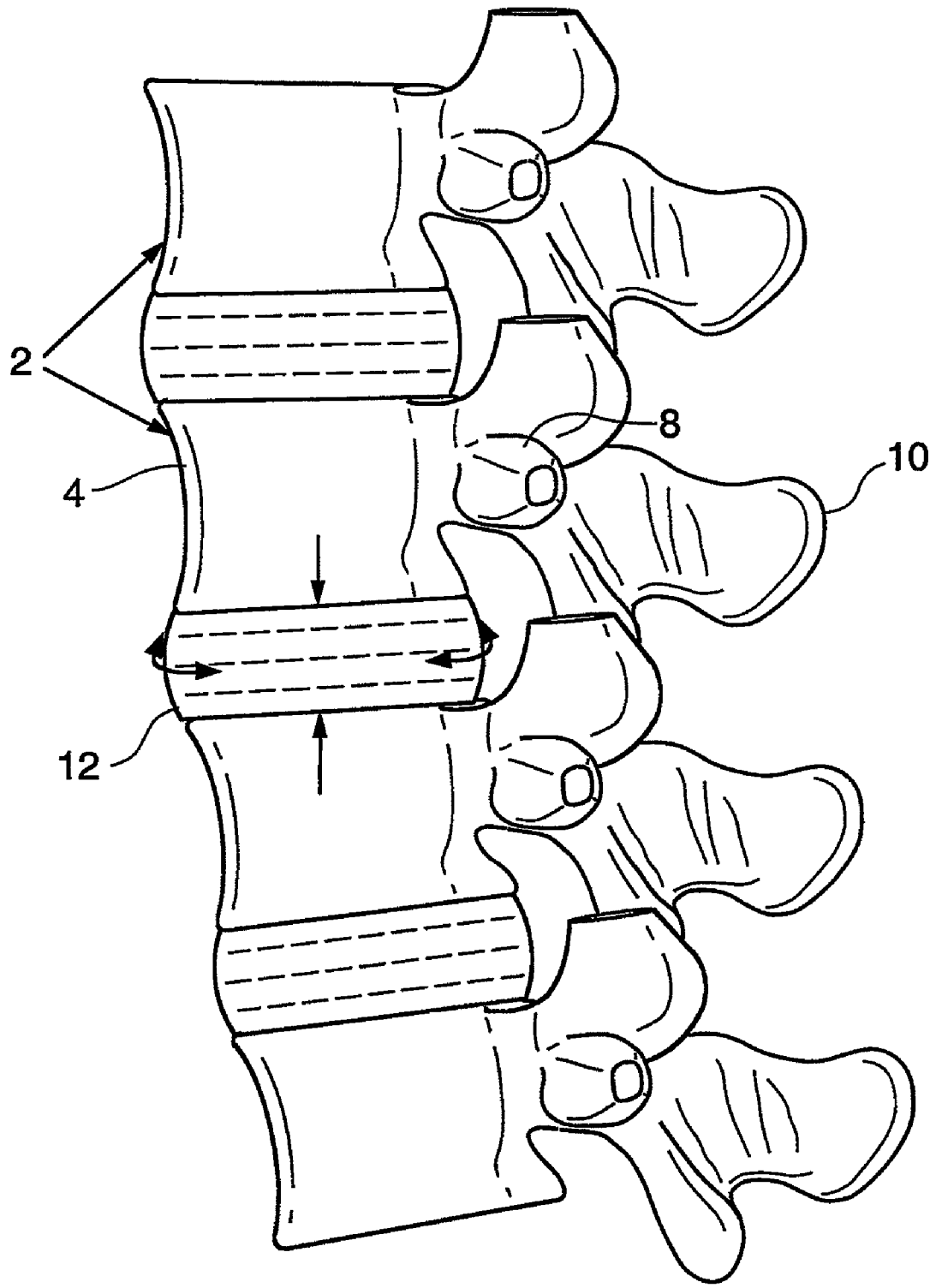
FIG. 1A is a schematic view of a portion of a human lumbar spine illustrating the spine under normal loading.

FIG. 1A illustrates a portion of the lumbar region of a human spine. As shown, the spine includes five lumbar vertebrae 2. Each of the vertebrae 2 has a vertebral body 4, lateral projections known as transverse processes 8, and a posterior projection called the spinous process 10. The vertebral bodies 4 are separated from one another by intervertebral discs 12. Each disc includes a nucleus pulposus, a semi-gelatinous tissue in the center of the disc surrounded and contained by the highly innervated annulus fibrosus, a circumferential band of tissue that prevents this material from protruding outside the disc space.

Figure 1B:
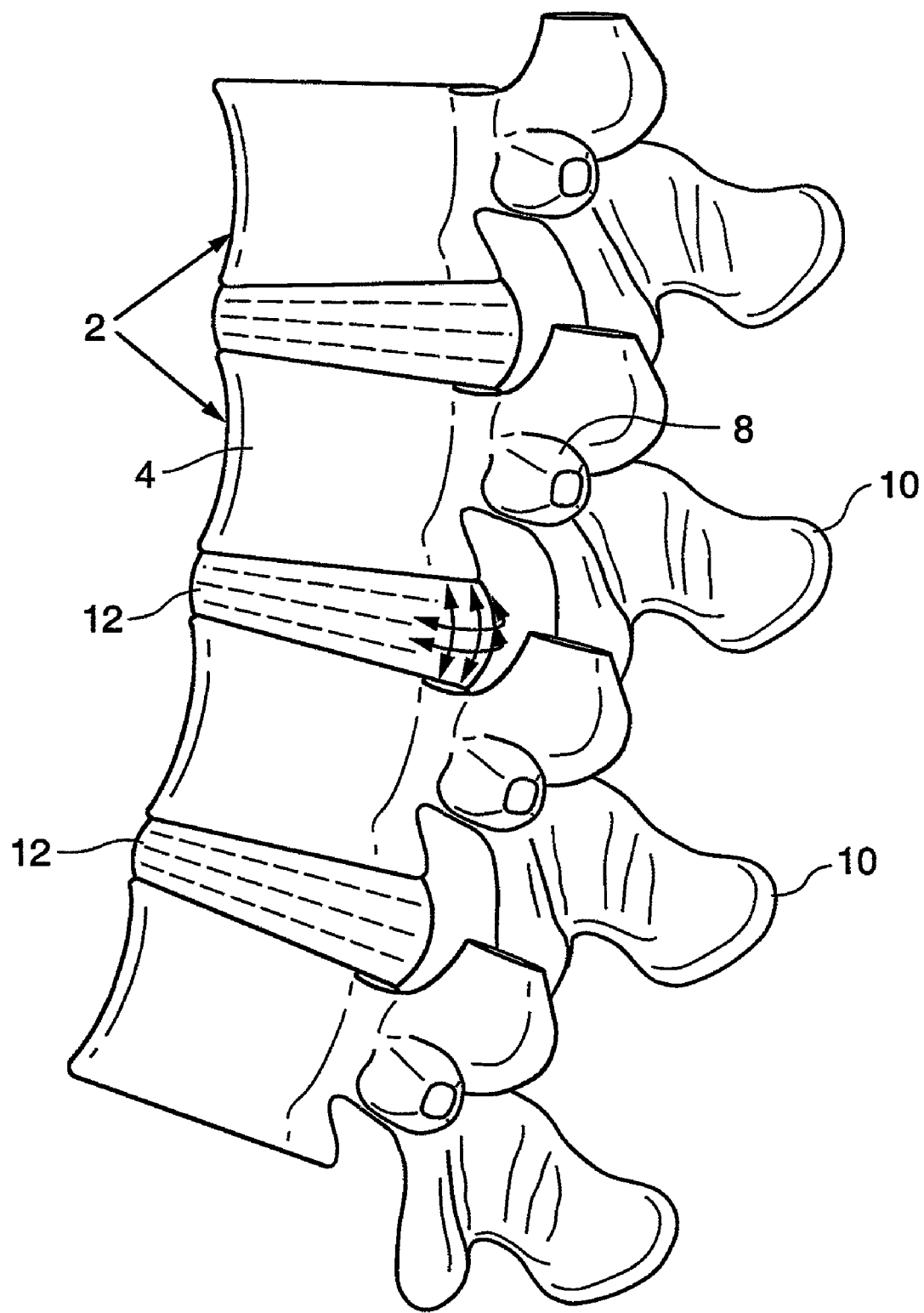
FIG. 1B is a schematic view similar to FIG. 1A illustrating the spine in flexion.

Under normal loading the lumbar spine curves forward as shown in FIG. 1A. In this condition, the discs 12 are subjected to axial forces by the vertebral bodies. Accordingly, the nucleus pulposus is under compression, while the annulus fibrosis experiences circumferential hoop stresses. However, when the lumbar spine is placed in flexion as shown in FIG. 1B (such as when the patient bends forward or sits), the disc experiences axial forces as well as forward bending forces. The bending forces displace nucleus polposus material dorsally, causing the anterior portion of the disc to be slightly compressed while the posterior portion of the disc is slightly expanded as shown. As a result, the dorsal region of the annulus is placed in tension, causing the patient to experience pain.

As can be seen by comparing FIGS. 1A and 1B, the spinous processes 10 spread apart from one another when the lumbar spine is under flexion. Several of the embodiments described herein restrict this spreading as a means for restricting flexion. In particular, FIGS. 2-8A illustrate embodiments of spinal implants for coupling two or more spinous processes of the lumbar vertebra as a means for restricting flexion of the lumbar spine so as to minimize lumber pain. It should be noted that although these embodiments are described in the context of the lumbar spine, they may be equally useful in the cervical spine. Moreover, the devices and methods described herein may be adapted for use in other areas of the spine and elsewhere in the body. For example, the devices may be implanted at alternative locations in the body where they may function as artificial ligaments, and the adjustment methods described herein may be used for adjusting artificial ligaments.

Figure 2:
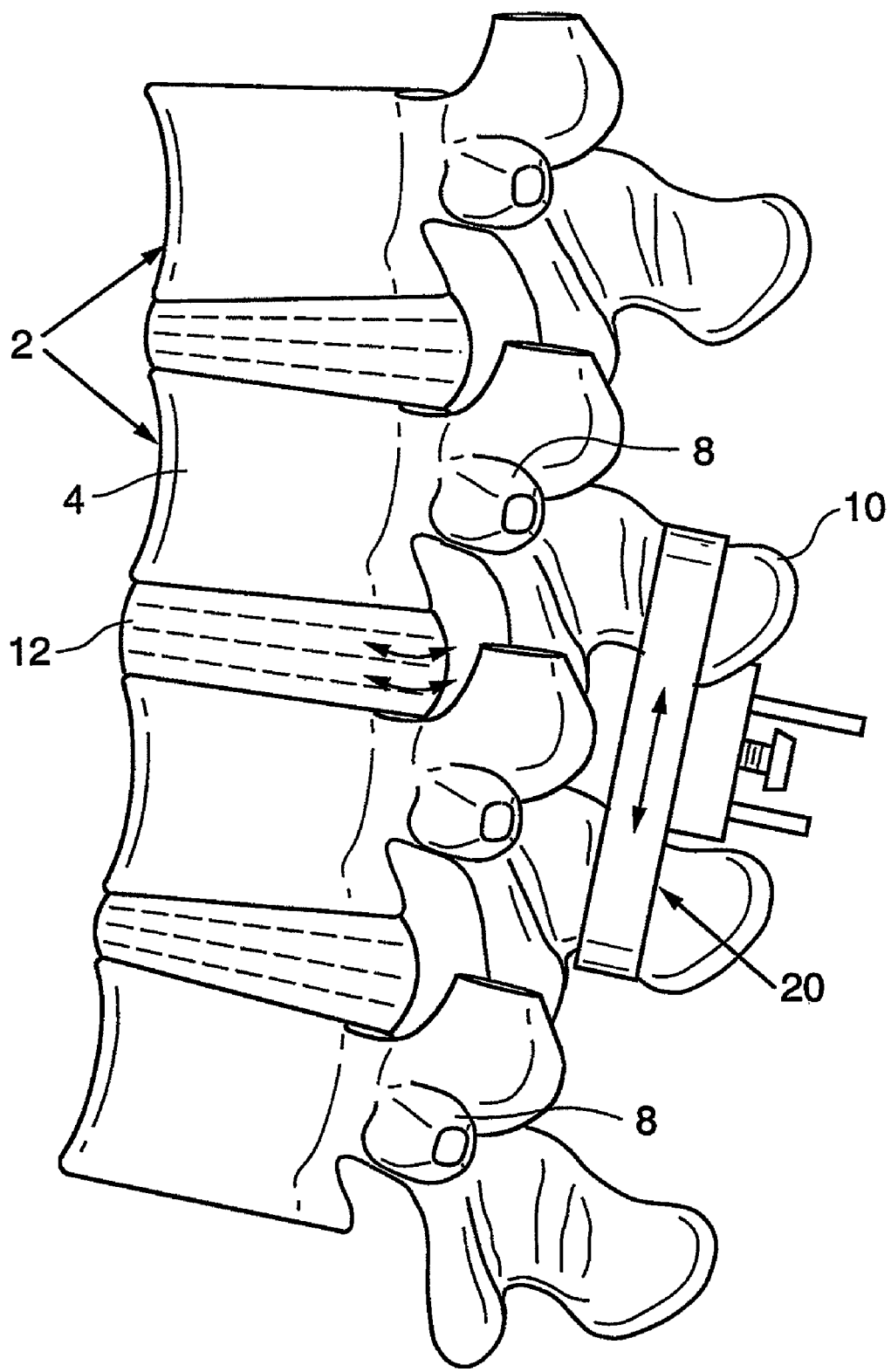
FIG. 2 is a schematic view similar to FIG. 1A illustrating a first embodiment of a spinal implant positioned around adjacent spinous processes.

Referring to FIG. 2, a first embodiment of a spinal implant comprises an elastic or semi-elastic band 20 sized to be positionable around adjacent spinous processes 10. Once implanted, the band 20 limits the amount of spreading between spinous processes 10 upon spinal flexion. Thus, when the patient bends the band 20 is placed in tension, thereby restricting posterior tension that would otherwise be experienced by the dorsal annulus and limiting the amount of flexion that can be achieved. Thus, the intervertebral disc is subjected to limited bending forces and pain is therefore reduced or eliminated. In this capacity, the band functions as an artificial ligament, supplementing the supraspinous and interspinous ligaments, which are normally loaded during flexion.

Figure 3C:
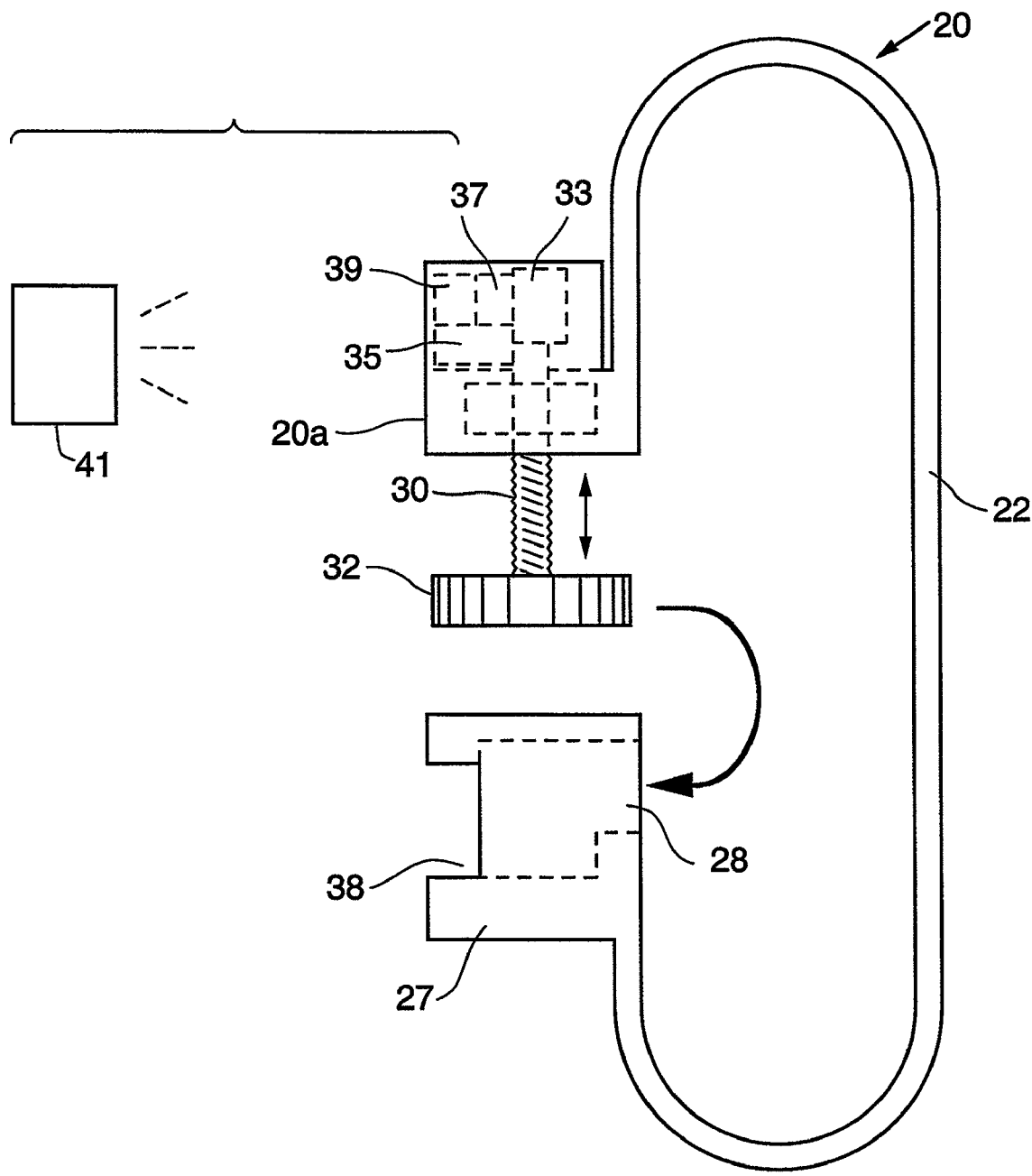
FIG. 3C is a side elevation view of the spinal implant of FIG. 2 in an opened position, and slightly modified to include motorized tension/length adjustment and an extracorporeal transmitter for controlling tension/length adjustments.
Figure 3D:
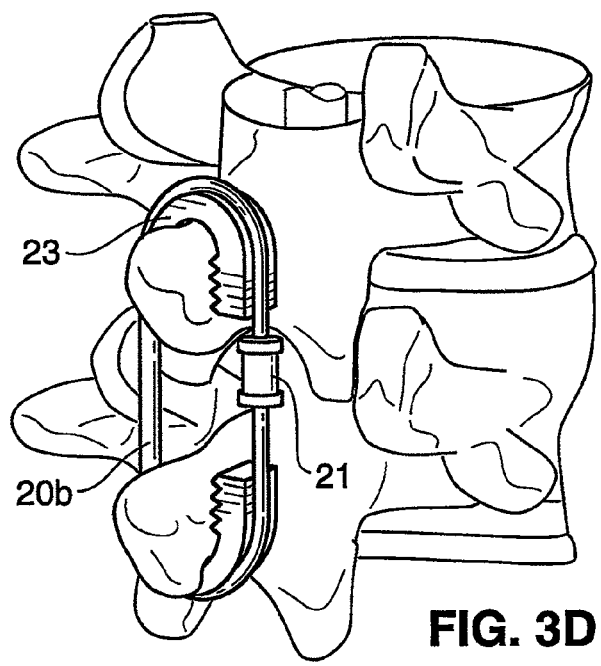
FIG. 3D is a perspective view of an implant similar to the implant of FIG. 2, but using a turnbuckle style connector.
Figure 5A:
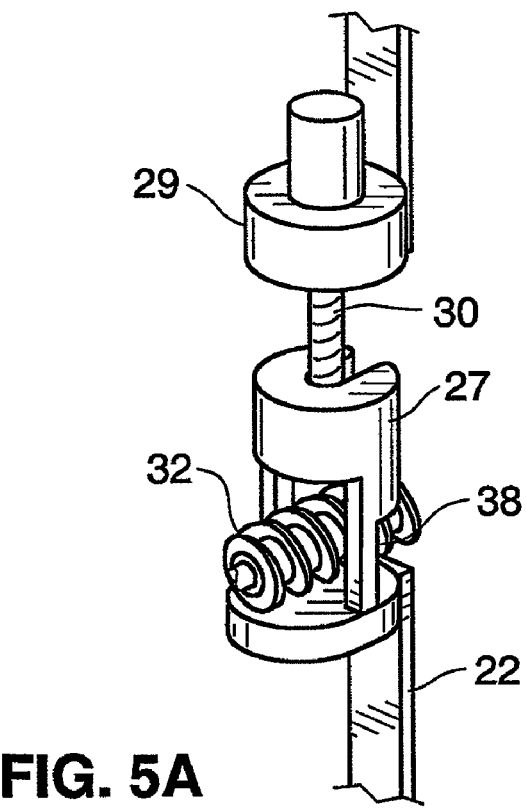
FIG. 5A is a perspective view of the FIG. 2 embodiment illustrating an access window for a worm screw adjustment mechanism.
Figure 6:
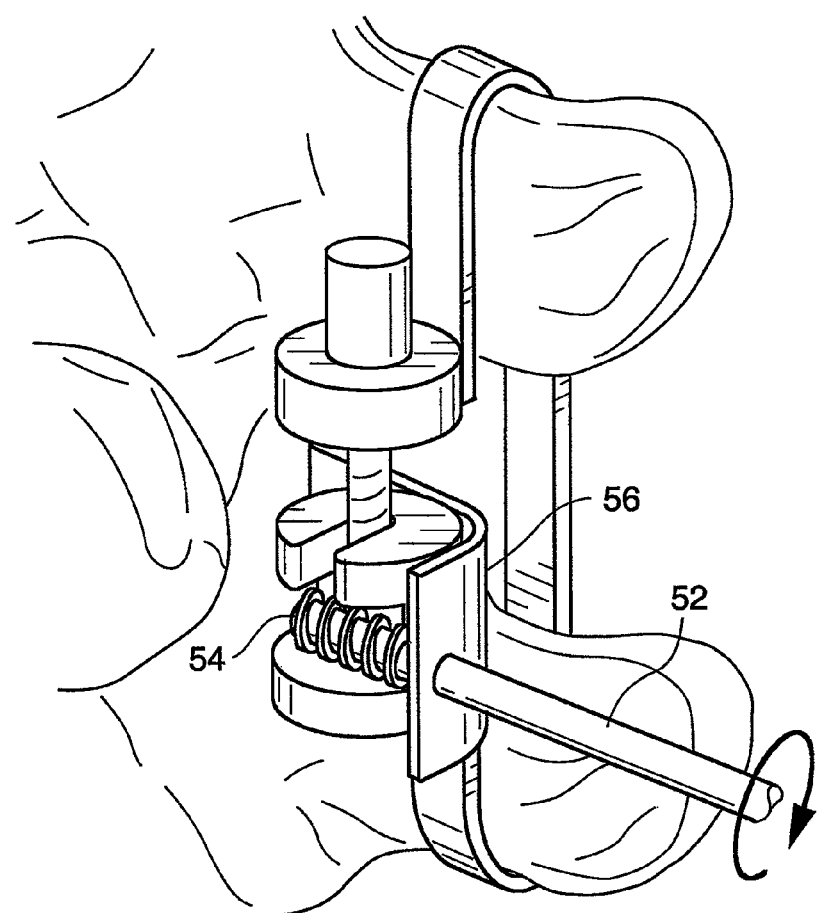
FIG. 6 is a schematic illustration of a human lumbar spine illustrating use of the adjustment tool of FIG. 5B on the spinal implant of FIG. 5A.

As best shown in FIG. 3A, band 20 includes an elongate portion 22 having ends 24a, 24b and a connector 26 for coupling the ends 24a, 24b to form the band into a loop. The connector 26 includes a housing 27 having a keyway opening 28 at end 24a, and a threaded rod or screw 30 extending from end 24b. It should be noted that in FIGS. 3A and 3B the band is partially twisted to cause keyway opening 28 to face outwardly so that it may be more easily seen and described. However, when the band is implanted the connector preferably faces inwardly as shown in FIGS. 3C, 5A and 6.

Threaded rod 30 includes a broadened head 32 that is receivable in the keyway opening 28. To engage the ends 24a, 24b, broadened head 32 is inserted into the keyway opening as indicated by arrow X, and then drawn upwardly as indicated by arrow Y to seat broadened head 32 within the housing 27 as shown in FIG. 3B. In an alternative embodiment, the rod 30 may be replaced by an alternative rod (not shown) that extends longitudinally from end 24b for streamlined implantation but that includes an end portion pivotable laterally to form a "T" shaped member. To close the loop, the cross member of the "T" is moveable into engagement with a keyway or other receiver on end 24a.

The connecting mechanism 26 illustrated in FIGS. 3A and 3B is particularly useful in that it allows the effective length of the band to be adjusted as needed by the surgeon. Referring again to FIG. 3A, the threads of rod 30 are engaged within corresponding threads of a captive nut 34 retained within a bore 36 in a housing 29 at connector end 24b. The rod 30 may be longitudinally advanced or retracted within the bore 36 by axially rotating the rod in a clockwise or counter-clockwise direction, such as by manually turning the head 32 using the thumb and forefinger. This allows the physician to adjust the effective length and degree of tension of the implant 20 prior to and/or after implantation. In an alternative embodiment, the device may include multiple adjustment assemblies to allow for gross adjustment as well as fine tuning of the device length and tension. Moreover, the implant may be formed of multiple elements (e.g. having multiple straps, connectors, and/or adjustment mechanisms) that come together to form the band.

Various other types of connecting mechanisms may be used to connect the ends of the band to form a loop. In an alternative embodiment shown in FIG. 3D, a tumbuckle nut 21 has internal threads engageable with threaded members located at the free ends of band 20a. The free ends of the band 20a include opposite thread patterns so that rotation of the tumbuckle in one direction draws the ends towards one another to shorten the loop, whereas rotation in the opposite direction spreads the ends away from one another to lengthen the loop. Other types of connecting mechanisms that may be used to form the band into a loop include hooks, crimp, zip tie type configurations, housing and set screw assemblies, hand-tied or instrument-tied knots or any other form of suitable connector.

Figure 3E:
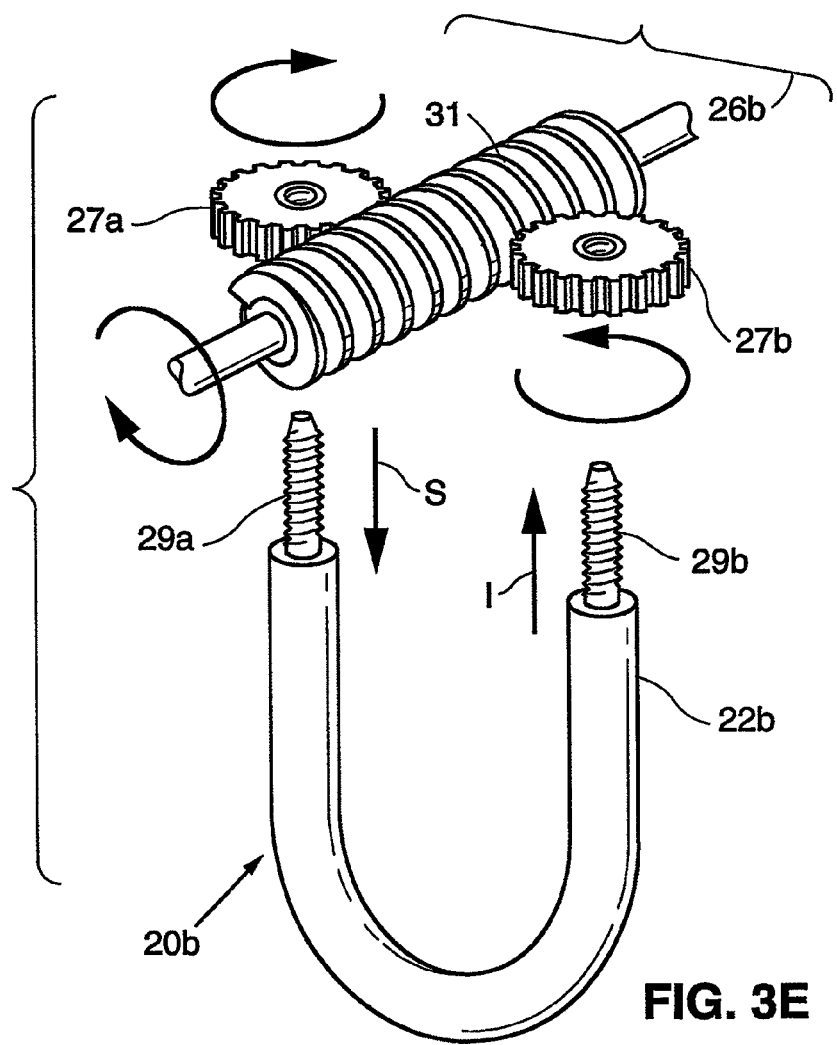
FIG. 3E is an exploded perspective view of another implant similar to the implant of FIG. 2, but using yet another alternative connector arrangement.

Another example, illustrated in exploded perspective view in FIG. 3E, includes a connector 26b having two threaded worm gears 27a, 27b and a worm screw 31. The threaded worm gears 27a, 27b receive corresponding threaded rods 29a, 29b, each of which is coupled to an end of a U-shaped body 22b of the band 20b as shown. When implanted, the band 20b is preferably oriented such that connector 26b is positioned above the superior spinous process (as shown) or below the inferior spinous process and such that the rods 29a, 29b extend in a generally axial direction next to and parallel to the sides of the spinous process. The worm screw and the threaded worm gears are arranged such that rotation of the worm screw in one direction effectively lengthens the band 20b by causing the worm gears to move along the rods in a superior direction (see arrow S), and such that rotation of the worm screw in the opposite direction effectively shortens the band by causing the worm gears to move along the rods in an inferior direction (see arrow I). Thus, the connector 26b allows a single worm gear within the connector assembly to simultaneously adjust both ends of the band to tighten or loosen the full band. The connector is preferably partially enclosed within a housing (not shown), with worm screw 31 exposed for access by a user.

Although in the FIG. 3A through FIG. 3E embodiments the ends of the band include components that engage with one another to form the loop connection, other configurations are possible. For example, the ends of the band may be drawn together and anchored together using a separate coupling device. A spring-loaded cord lock having a hole which receives the ends of band and which allows the band to be "cinched" around the spinous processes is one example. As another example, a single end of the band may include a coupling device which can receive and engage the opposite free end of the band. Naturally, many alternative configurations are conceivable.

Referring again to the preferred embodiment of FIG. 3A, the elongate portion 22 of the band 20 is preferably made of a biocompatible elastic or semi-elastic material selected to restrict flexion of the lumbar spine by a desired degree (e.g. an amount sufficient to relieve pain) by increasing the stiffness of the effected joint segment (e.g. L4/L5) by some amount, which may vary for different patients. In one embodiment, the spring constant of the device would be 25-75 N/mm. In a preferred embodiment, flexion is not completely inhibited, but is instead limited only within the range in which flexion causes pain or significant pain, while rotation and extension are incidentally and only minimally restricted by placement of the band. Suitable examples of materials include (but are not limited to) single monofilament elastic materials in tension (e.g. elastomers or suitable biocompatible materials such as those manufactured by Polymer Technology Group of Berkeley, C A), polyurethanes, polycarbone/polyether urethanes, thermoplastic silicone urethane copolymers, metal springs (e.g. stainless steel or NiTiNOL, coiled or otherwise, in tension or compression), knit or woven materials. If desired, the interior surface of the band may have properties for preventing slipping between the band and adjacent bone, and/or for promoting ingrowth of bone material or other tissue ingrowth that facilitates retention of the band. For example, the interior surface of the band may include gripping elements or surface roughness, or a porous in-growth-promoting surface. Alternatively, supplemental elements may be combined with the band 20 to prevent slipping, such as the elements 23 shown in FIG. 3D. Such elements may be pre-attached to the band or separately placed in contact with the spinous process during implantation to prevent slipping.

In an alternative embodiment, suitable bioresorbable materials may alternatively be used for some or all of the components.

Figure 4A:
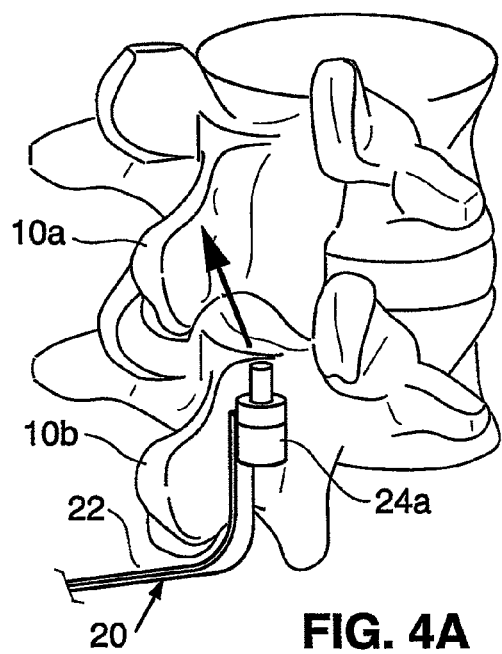
FIGS. 4A through 4D are a sequence of views of a human lumbar spine illustrating a sequence of steps for implanting the spinal implant of FIG. 2.
Figure 4B:
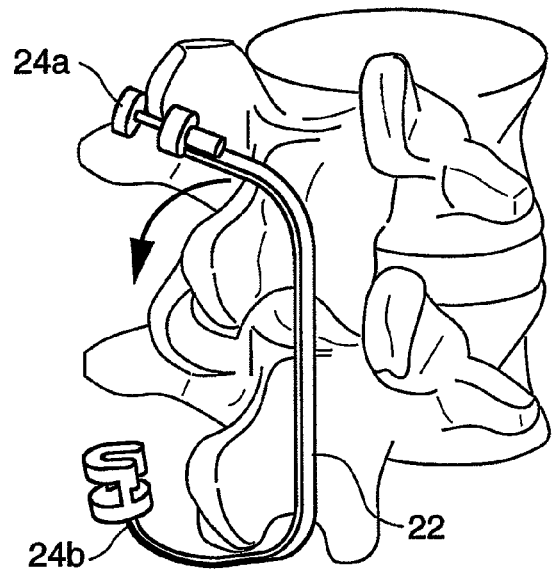
Figure 4C:
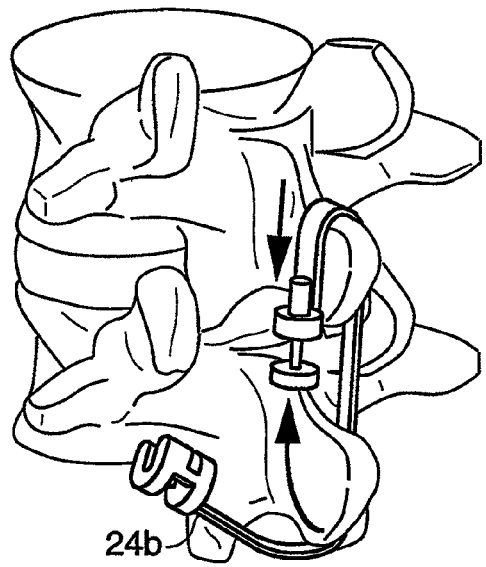
Figure 4D:
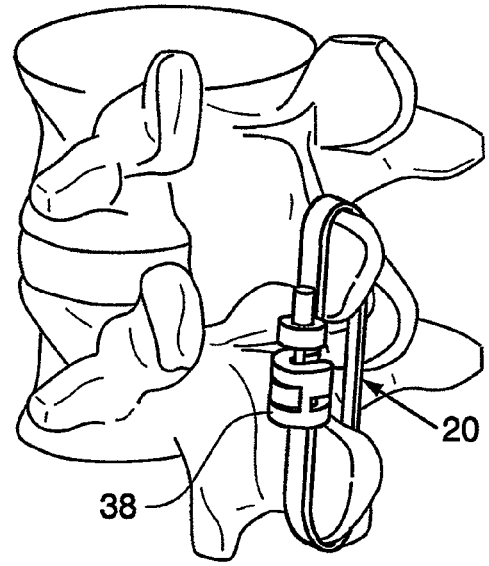

One method for implanting the band 20 of FIG. 2 will next be described. Implantation may be carried out using surgical techniques via a midline incision, or minimally invasively through a keyhole incision. After penetration through the fascia, the muscle next to the spinous processes is distracted to give the surgeon access to the spinous processes and interspinous ligaments. Two holes may be pierced in the interspinous ligaments to facilitate implantation of the device: one in the interspinous ligament above the superior spinous process and one in the interspinous ligament below the inferior spinous process. Prior to positioning of the band 20, the effective length of band may optionally be adjusted by rotating threaded rod 30 to increase or decrease its effective length as described above. FIGS. 4A through 4C illustrate one example of a method for implanting the band 20. According to this exemplary method, one end 24a of the band 20 is passed through the incision and advanced superiorly until it is positioned adjacent to the desired pair of spinous processes 10a, 10b. FIGS. 4A and 4B. One or both ends of the band 20 are wrapped around the spinous processes 10a, 10b and brought towards one another as shown in FIG. 4C. If the spinal segment of interest is one at which there is a spinous process that is inadequate or otherwise shaped in a manner that will prevent it from retaining the band, the spinous process may be engaged by the band in an alternative way. For example, a small hole may be formed in that spinous process and the band may be passed through the small hole. This approach may be particularly desirable where a band is to be placed at the L5-S1 segment.

The head 32 is inserted into the keyway opening to engage the ends 24a, 24b. If the surgeon determines that the band 20 is too loose to adequately restrict flexion or too tight to permit an appropriate amount of flexion, adjustments to the effective length of rod 30 may be made at this time. As is clear from the description, the band is preferably held in place without the use of screws, nails, or other attachment devices penetrating the bone or cemented to the bone—although in some circumstances it may be desirable to utilize such means of attachment to facilitate retention.

As discussed above, the implanted band 20 limits the amount of spinal flexion without significantly restricting rotation or extension of the spine. If necessary for the patient's condition, multiple bands may be used at multiple segments within the spine.

As discussed previously, band 20 preferably includes features for adjusting the effective length of the band, such as by rotating the threaded rod 30 to cause it to screw further into or out of the captive nut 34. It is further preferable to provide features that permit this type of adjustment both immediately following implantation and in a later procedure if desired.

Figure 5B:
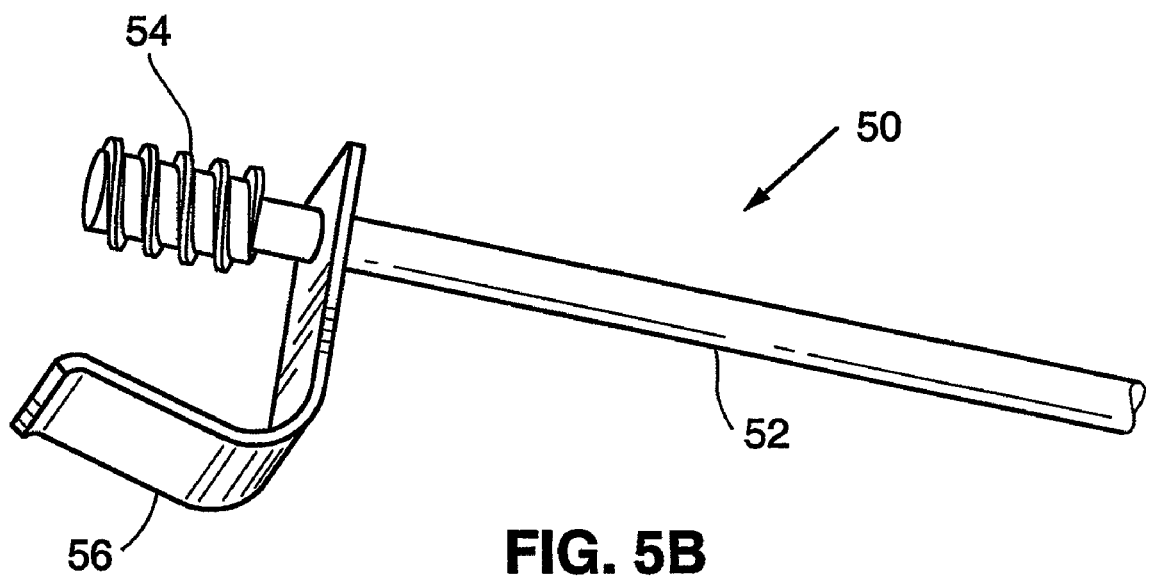
FIG. 5B is a perspective view of an adjustment tool engageable with implant of FIG. 2 for using in adjusting the effective length of the band.

Referring to FIG. 5A, the broadened head 32 of the threaded rod 30 may take the form of a worm gear having teeth along its exterior edges. When the band is assembled, a portion of the worm gear 32 is exposed through a window 38 in housing 27. Referring to FIG. 5B, a suitable adjustment tool 50 includes an elongate rod 52 and a threaded member 54 that is engageable with the exposed threads on the worm screw 32. An L-shaped spring clip 56 extends laterally from the rod 52.

Referring to FIG. 6, to adjust the length of the band 20, the tool's threaded member 54 is engaged against the corresponding threads of the worm gear 32, while the spring plate 56 is positioned in contact with an opposite side of the housing 27 to steady the tool 50 against the implant. When the threaded member of the adjustment tool is turned, it rotates the worm gear 32, causing the threaded rod 30 to move up or down through the captive nut, thereby lengthening or shortening the effective length of the band as shown in FIG. 6. As discussed, this adjustment may be carried out immediately following positioning of the band 20, or during a separate procedure at a later date if it is determined that increased or decreased restriction is desired. The tool 50 could be threaded through a small incision to gain access to the implanted device.

Naturally, many other mechanisms for adjusting the effective length of the band before and/or after implantation may be provided. These mechanisms may be operatively associated with the band's connecting mechanism, or they may be entirely separate from the band's connecting mechanism. One example includes the turnbuckle arrangement shown in FIG. 3B, in which the turnbuckle nut 21 may be rotated in one direction to tighten the loop or rotated in the other direction to loosen the loop. Other examples include hose-clamp type mechanisms, ratchet configurations or screw mechanisms that may be adjusted using adjustment tools (e.g. screwdrivers, ratcheting devices etc.), piston elements that expand or contract upon addition or removal of a fluid (e.g. air or liquid) into or from a reservoir using a syringe, shape memory elements or other elements having material properties that will allow for an effective change in response to changed environmental conditions (e.g. electrically or thermally activated length changes initiated by application of heat or electricity using a conductor positioned adjacent to or into contact with the band, or chemically activated length changes using a chemical agent passed into contact with the band using a syringe or catheter). Links or other elements that may be added/removed to increase/decrease the band's length, or lengths of elastic material forming the band may be wrapped on a spool and payed out or coiled up to effect length changes in the band. As another example, sections of the band material may be displaced transversely to shorten the effective length of the band.

Referring to FIG. 3C, the band 20 may be equipped with a motor 33 and battery 35 for effecting band length changes by driving the rod 30, together with electronic components 37 that control the motor. Although one arrangement of components is illustrated in FIG. 3C, many others are possible, including one in which the motor drives the head 32 of the threaded rod 30.

Additional electronics 39 may allow length changes to be accomplished non-invasively. For example, the electronic components 39 may include receivers for radio, optical, or magnetic signals transmitted through the skin. These components may be housed within housing 29a with the motor coupled to threaded rod 30. The device would thus be programmed to adjust the band length in response to transcutaneous signals received from an external device 41. The band's electronics 39 may further include transmitters for transmitting data indicating the current length and/or tension setting for the implant to the external device 41. In a similar embodiment, the band may be coupled to one or more buttons palpable through the skin that can activate the motor for length adjustments. The buttons may be positioned directly on the band or in a subcutaneous pocket. In other embodiments, the band may be manually adjusted by manipulating an actuator (e.g. a rotatable knob) palpable through the skin. In other embodiments, the band may be adjusted by passing a magnet over the skin in order to mechanically manipulate an element under the skin via the magnetic field. In other embodiments, a motorized pump may pump fluid to or from a piston chamber to affect a change in loop length. Transcutaneous length adjustments are also possible using embodiments of the type above for which a syringe may be used as an adjustment tool (e.g. for injecting fluid into a piston chamber or for injecting a chemical agent into contact with a chemically material that changes shape in response to chemical exposure), by passing the syringe through the skin to the target location. A tatoo or other visual marker may be positioned on the skin to allow the physician to easily identify the target injection site.

Figure 7:
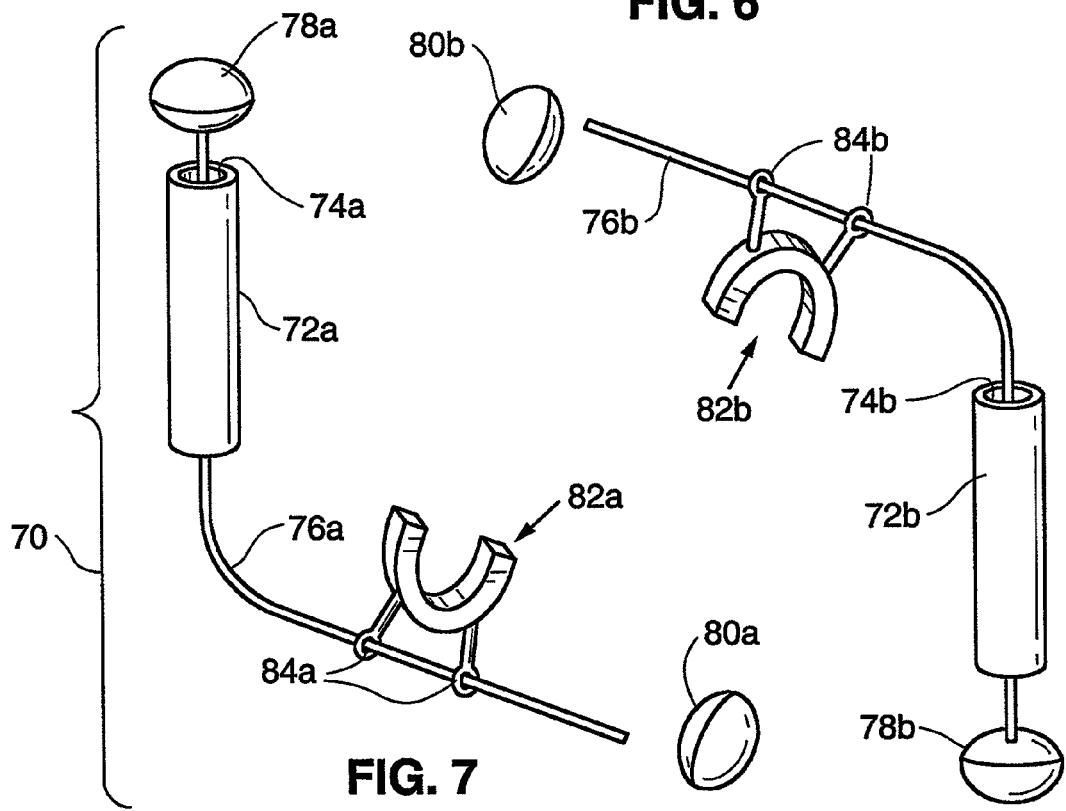
FIG. 7 is a perspective view of components of a third embodiment of a spinal implant.

Components of a third embodiment of a spinal implant 70 are illustrated in FIG. 7. Implant 70 is similar to the prior embodiments in that, when assembled, it takes the form of a band positionable around the spinous processes. However, it differs from prior embodiments in that it restricts spinal flexion using compression elements that are placed in compression upon expansion of the band during spinal flexion.

Referring to FIG. 7, implant 70 includes a pair of elastomeric members 72*a*, 72*b*, each of which includes a throughbore 74*a*, 74*b* and a cable 76*a*, 76*b* extending through the throughbore. Cables 76*a*, 76*b* are preferably inelastic, although in an alternative embodiment elastic cables may also be used. The elastomeric members may be housed in an enclosure or casing 86 (FIG. 9) formed of a biocompatible metal (e.g. titanium or stainless steel) or polymer, if desired. Casing 86 includes a removable cap 88 which mates with the casing using threaded connections. Openings 89*a*, 89*b* are provided in the casing 86 and cap 88 for passage of the cables 76*a*, 76*b*.

Figure 9:
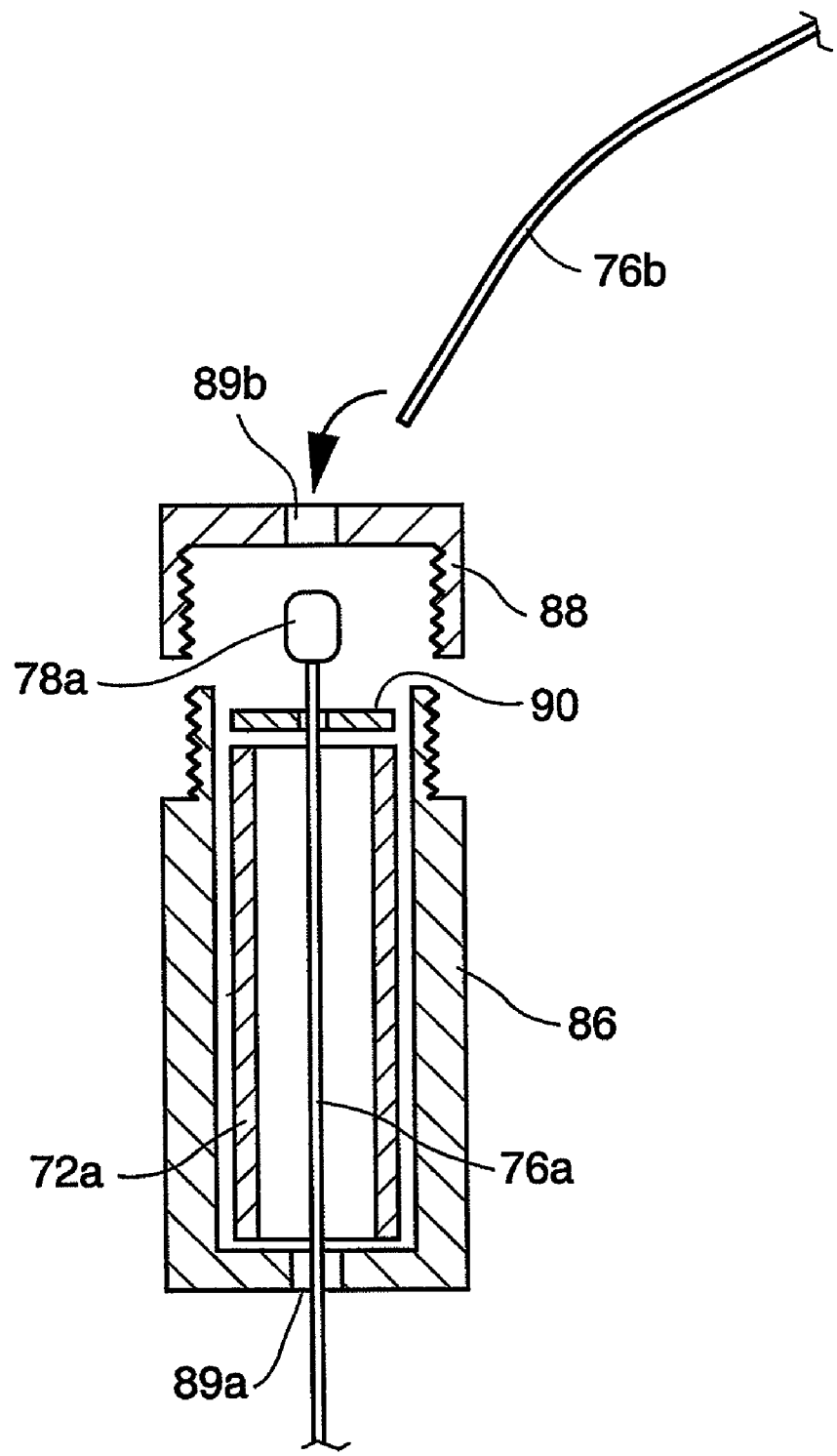
FIG. 9 is an exploded view of a housing assembly for a compression member of the embodiment of FIG. 7

Each cable preferably includes a first stopper element 78*a*, 78*b* fixed to one of its ends, and a second stopper element 80*a*, 80*b* attachable to its free end. If the casing 86 of FIG. 9 is used, a washer 90 may be positioned between each stopper element 78*a* and its corresponding elastomeric member 72*a*.

The stopper elements 78*a*, 78*b*, 80*a*, 80*b* are proportioned such that they cannot pass through the throughbores 74*a*, 74*b*. The implant 70 further includes a pair of arcuate elements 82*a*, 82*b*, each of which includes receiving elements such as loops 84*a*, 84*b* on its convex side as shown. Each of the cables 76*a*, 76*b* extends through the loops of one of the rigid arcuate elements 82*a*, 82*b*. During use, the arcuate elements 82*a*, 82*b* are positioned in contact with the spinous processes where they may prevent slipping between the band and adjacent bone. The elements 82*a*, 82*b* may also utilize materials or coatings that will promote tissue ingrowth that facilitates retention of the band. The elements 82*a*, 82*b* may also provide a track through which the band passes. Although the elements 82*a*, 82*b* are shown as being arcuate, they may have other shapes without departing from the scope of the invention.

Figure 8A:
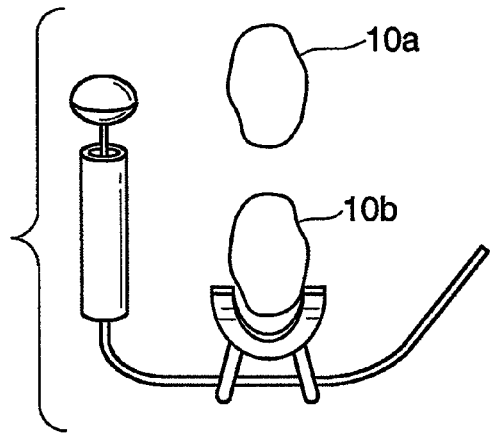
FIGS. 8A through 8D illustrate a sequence of steps for implanting the embodiment of FIG. 7.
Figure 8B:
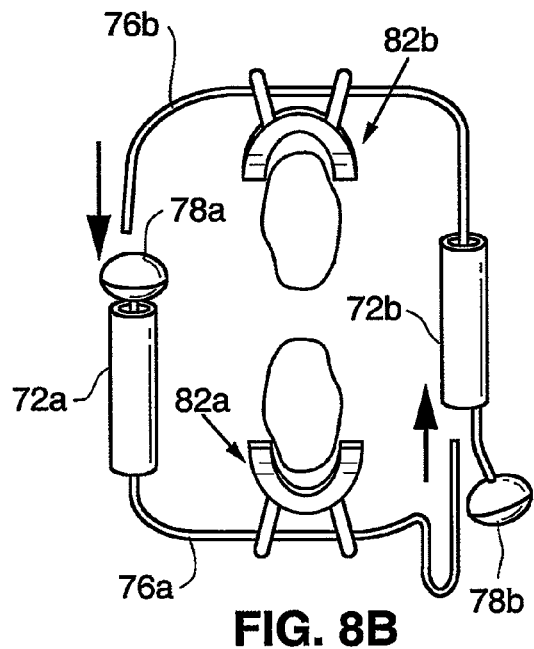
Figure 8C:
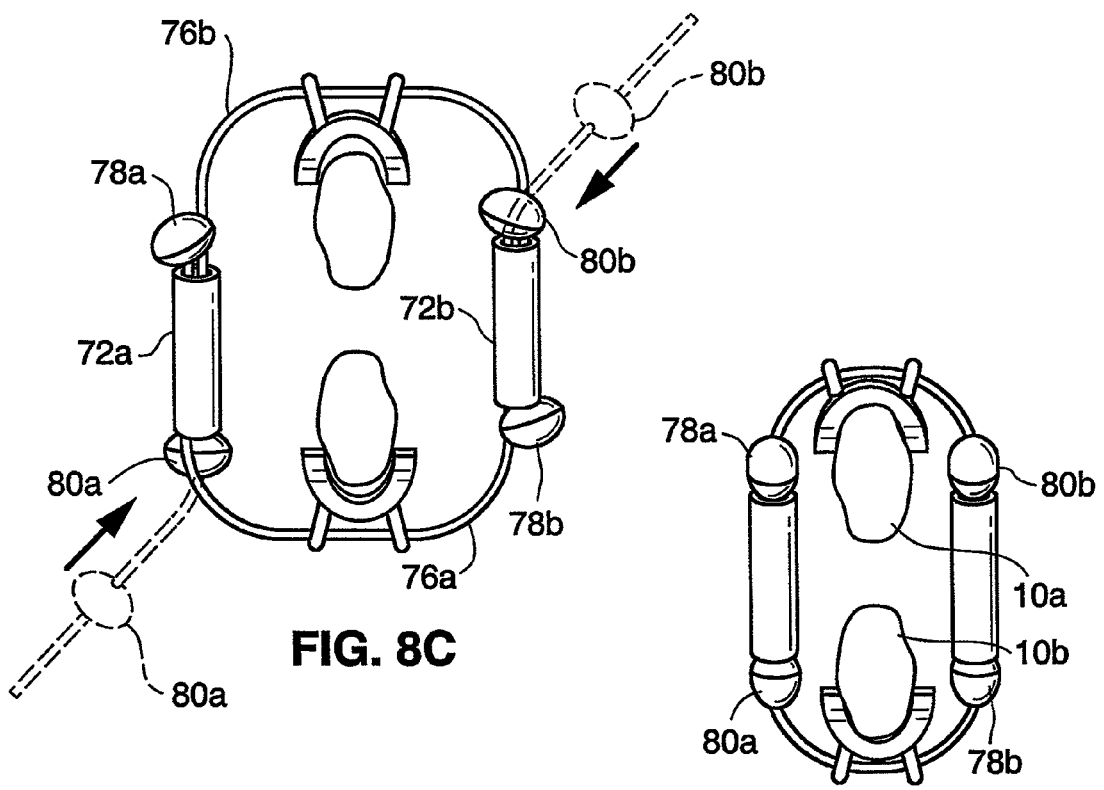
Figure 8D:
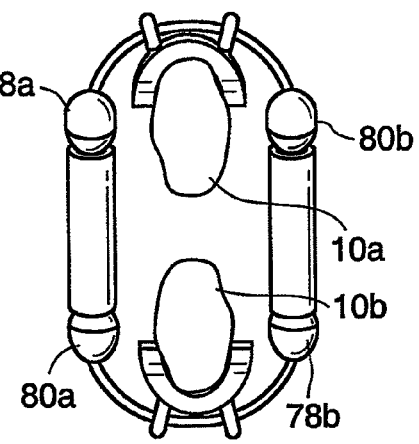

A method for positioning the implant 70 will next be described with reference to FIGS. 8A through 8D. For simplicity, only the posterior sides of the spinous processes 10 involved in the procedure are shown. Prior to implantation, each cable is preferably preassembled with its corresponding arcuate element and elastomeric member. Referring to FIG. 8A, a first one of the cables 76*a* is positioned with its arcuate element 82*a* positioned with its concave side facing a spinous process 10*a*. The second cable 76*a* is similarly introduced at the other spinous process 10*b*, and the free end of each cable 76*a*, 76*b* is threaded through the elastomeric member 72*a*, 72*b* of the opposite cable as shown in FIG. 8B. Finally, the remaining stoppers 80*a*, 80*b* are mounted to the free ends of the cables as shown in FIG. 8C, causing each of the elastomeric members to be positioned between and in contact with a pair of the stoppers. The cables are tightened around the spinous process as shown in FIG. 8D, and the stoppers are locked in place (such as by crimping or other action) to retain the cables in the tightened configuration.

As discussed previously, flexion of the spinal segment will cause the spinous processes 10*a*, 10*b* to spread away from one another. When the implant 70 is positioned as shown in FIG. 8D, spreading of the spinal processes will impart expansive forces to the implant 70. These expansive forces cause each of the elastomeric members 72*a*, 72*b* to be compressed between a pair of the stoppers 80*a*, 80*b*, 78*a*, 78*b*, thereby restricting expansion of the implant 70 and thus limiting spinal flexion at the segment in which the implant is positioned. Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

What is claimed is:

1. A method for restricting flexion of a spinal segment in a patient, said spinal segment comprising a first vertebra having a first spinous process and a second vertebra having a second spinous process, wherein said spinous processes are separated by a space and the spinal segment undergoes extension and flexion causing the spinous processes to move into and away from the space respectively, said method comprising:
   positioning a first inelastic cable over a superior surface of the first spinous process;
   positioning a second inelastic cable under an inferior surface of the second spinous process;
   positioning a first elastic member along one side of the space between the spinous processes; and
   positioning a second elastic member along an opposite side of the space between the spinous processes;
   wherein first ends of the first and second inelastic cables are connected to opposite ends of the first elastic member respectively and second ends of the first and second inelastic cables are connected to opposite ends of the second elastic member respectively so that the elastic members and inelastic cables form an elastic band which limits flexion of the segment as the spinous processes move away from the space when undergoing flexion.

2. A method as in claim 1, further comprising selecting a patient having lumbar pain exacerbated by spinal flexion.

3. A method as in claim 1, further comprising assembling at least a portion of the elastic band prior to the positioning steps.

4. A method as in claim 3, wherein assembling comprises attaching a first end of the first inelastic cable to the first elastic member and a first end of the second inelastic cable to the second elastic member.

5. A method as in claim 1, wherein at least some of the cable(s) are pre-attached to the elastic member(s) prior to positioning.

6. A method as in claim 1, further comprising connecting connectors to attach the inelastic cables to the elastic members after positioning.

7. A method as in claim 6, further comprising adjusting adjustment mechanisms on the connectors to change an effective length of the elastic band.

8. A method as in claim 7, wherein the adjustment mechanisms are adjusted immediately after positioning and connecting the inelastic bands and the elastic members.

9. A method as in claim 7, wherein the adjustment mechanisms are adjusted in a separate procedure after the initial implantation procedure.

10. A method as in claim 1, further comprising retaining the first inelastic cable over the superior surface and the second inelastic cable under the inferior surface.

11. A method as in claim 10, wherein retaining comprises disposing elements between the inelastic cables and the surfaces to limit slipping.

12. A method as in claim 10, wherein retaining comprises promoting tissue ingrowth between the inelastic cables and the surfaces.

13. A method as in claim 1, wherein the first inelastic cable and the second inelastic cable are separately tightened around the adjacent spinous process.

14. A method as in claim 13, wherein the first cable is tightened by threading the first cable through the first elastic member and the second cable is tightened by threading the second cable through the second elastic member.

15. A method for restricting flexion of a spinal segment in a patient, said spinal segment comprising a first vertebra having a first spinous process and a second vertebra having a second spinous process, wherein said spinous processes are separated by a space and the spinal segment undergoes extension and flexion causing the spinous processes to move into and away from the space respectively, said method comprising:
    positioning a band over a superior surface of the first spinous process and under an inferior surface of the second spinous process, wherein the band includes an inelastic cable and at least one elastic member to limit flexion of the segment as the spinous processes move away from the space without significantly restricting rotation or extension of the segment, wherein the inelastic cable is attached to opposite ends of the elastic member; and
    adjusting the effective length of the band encircling the spinous processes so that the at least one elastic member elastically limits spreading of the spinous processes and flexion of the spinal segment.

16. A method as in claim 15, further comprising selecting a patient having lumbar pain exacerbated by spinal flexion, wherein the effective length of the band is adjusted to increase stiffness of a spinal segment within a range that minimizes lumbar pain.

17. A method as in claim 15, wherein adjusting is effected during an initial implantation procedure.

18. A method as in claim 17, further comprising adjusting in a separate procedure after the initial implantation procedure.

19. A method as in claim 18, wherein adjusting in the separate procedure comprises introducing a tool through a small incision.

20. A method as in claim 15, wherein adjusting comprises wrapping or paying out lengths of the band on a spool.

21. A method as in claim 15, wherein adjusting comprises adding or removing links from the band.

22. A method as in claim 15, wherein adjusting comprises transversely displacing a section of the band.

23. A method as in claim 15, wherein the adjusting step includes the step of introducing an adjustment tool percutaneously into contact with the band and using the adjustment tool to adjust the effective length.

24. A method as in claim 15, wherein the adjusting step includes the step of positioning a transcutaneous adjustment device outside the patient in proximity to the band, and using the adjustment device to control adjustment of the effective length.

25. A method as in claim 24, wherein the trancutaneous adjustment device is selected from the group consisting of telemetric, magnetic, optical, and radiofrequency control devices.

26. A method as in claim 15, wherein the band comprises a first inelastic cable positioned over the superior surface of the first spinous process and a second inelastic cable placed under the inferior surface of the second spinous process, wherein the cables are each connected to an elastic member on one side of the space and another elastic member on an opposite side of the space.

27. A method as in claim 15, further comprising retaining the band on the spinous processes.

28. A method as in claim 27, wherein retaining comprises disposing elements between the band and the spinous processes to limit slipping.

29. A method as in claim 27, wherein retaining comprises promoting tissue ingrowth between the band the spinous processes.

* * * * *